United States Patent [19]

Imran

[11] Patent Number: 5,330,466
[45] Date of Patent: Jul. 19, 1994

[54] CONTROL MECHANISM AND SYSTEM AND METHOD FOR STEERING DISTAL EXTREMITY OF A FLEXIBLE ELONGATE MEMBER

[75] Inventor: Mir A. Imran, Palo Alto, Calif.

[73] Assignee: Cardiac Pathways Corporation, Sunnyvale, Calif.

[21] Appl. No.: 983,963

[22] Filed: Dec. 1, 1992

[51] Int. Cl.$^5$ .............................................. A61M 37/00
[52] U.S. Cl. .................................... 606/13; 604/95; 604/280; 606/15
[58] Field of Search ............................. 604/95, 164–167, 604/170, 280–282; 606/13–15, 7, 46; 128/772, 656–658, 4, 6

[56] References Cited

U.S. PATENT DOCUMENTS 5,114,402  5/1992  McCoy ............................. 604/95

FOREIGN PATENT DOCUMENTS

WO9111213  8/1991  PCT Int'l Appl. .

*Primary Examiner*—Stephen C. Pellegrino
*Assistant Examiner*—M. Peffley
*Attorney, Agent, or Firm*—Flehr, Hohbach, Test, Albritton & Herbert

[57] ABSTRACT

A device compressing a flexible elongate member having proximal and distal extremities and having a plurality of circumferentially spaced-apart elements having a characteristic disposed in the distal extremity. A control mechanism is secured to the proximal extremity of the flexible elongate member. The control mechanism has a housing adapted to be grasped by a human hand. A first control member is slidably mounted in the housing. A second control member is rotatably mounted in the housing. The first and second control members are accessible to the fingers of the human hand grasping the housing. Electrical circuitry couples the first and second control members to the elements whereby when the first and second control members are moved, the distal extremity of the flexible elongate member is moved in accordance with the positioning of the first and second control members.

9 Claims, 4 Drawing Sheets

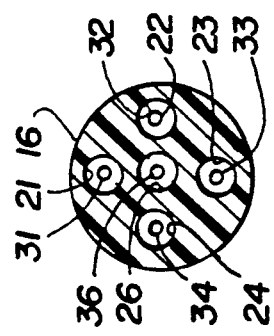
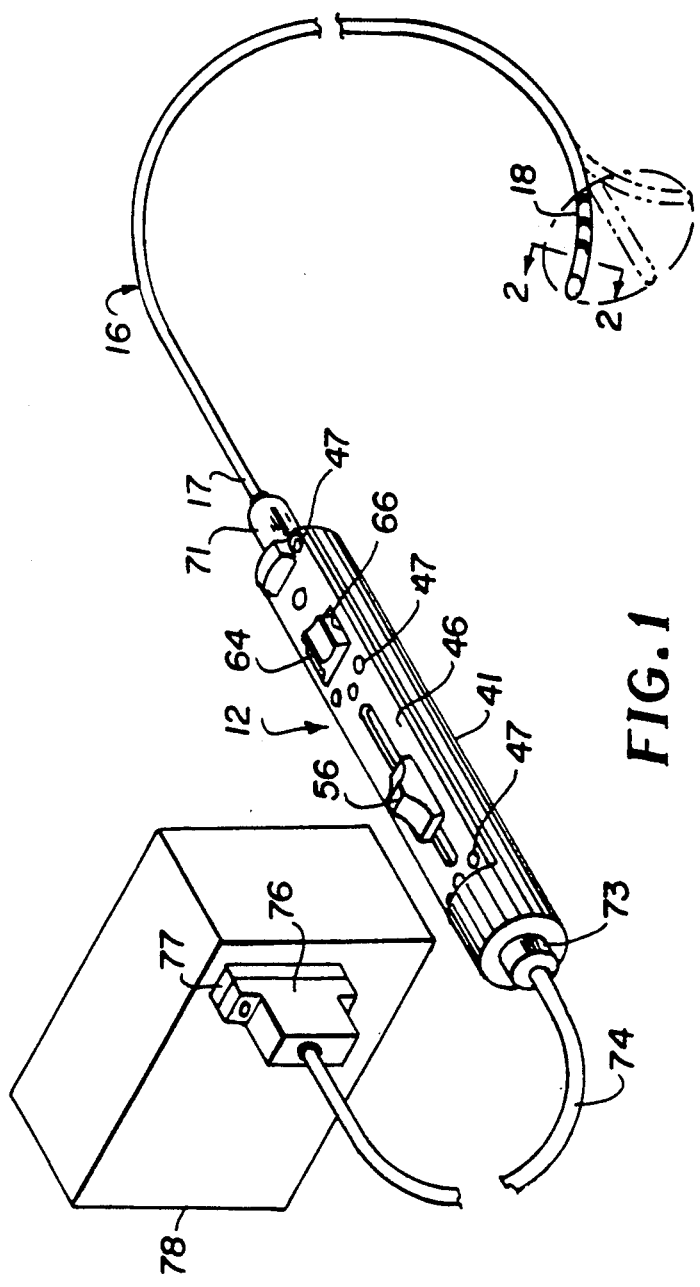
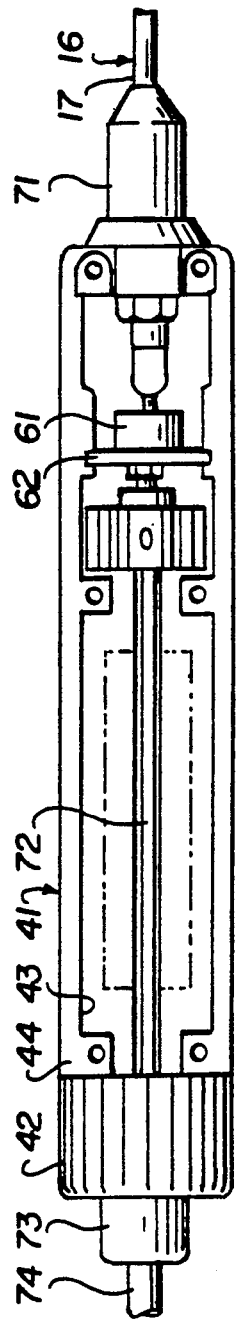

CONTROL MECHANISM AND SYSTEM AND METHOD FOR STEERING DISTAL EXTREMITY OF A FLEXIBLE ELONGATE MEMBER

This invention relates a control mechanism and system and method for steering the distal extremity of a flexible elongate member, as for example a catheter.

In U.S. Pat. No. 5,238,005, there is disclosed a joystick-type of control for controlling the distal extremity of a flexible elongate member. In certain applications, as for example in endocardial ablation, use of such a joystick control has been found to be undesirable because in such a joystick control it is necessary to hold the joystick in the desired position because as soon as it is released it normally returns to its home position typically under the force of springs. In an ablation procedure which may take a period of time, it is difficult to hold the joystick in the desired location for that period of time. Also, in conjunction with a joystick control, it has been found that it is difficult to make certain movements. For example, if it is desired to help the same bend in the distal extremity of the catheter but to move it a few degrees to the right or the left, this is difficult to do without changing the amount of bend in the distal extremity of the catheter. There is, therefore a need for a new and improved control mechanism, system and method for steering the distal extremity of a flexible elongate member.

In general, it is an object of the present invention to provide a control mechanism and system and method for steering the distal extremity of a flexible elongate member which facilitates retaining the distal extremity of the flexible elongate member in a predetermined position.

Another object of the invention is to provide a control mechanism, system and method of the above character which permits a small amount of movement of the distal extremity of the catheter in one direction without affecting the position of the distal extremity of the flexible elongate member in another direction.

Another object of the invention is to provide a control mechanism, system and method of the above character in which the desired motion for the distal extremity of the flexible elongate member is determined by first and second controls.

Another object of the invention is to provide a control mechanism, system and method of the above character in which the first control represents the amount of bend placed in the distal extremity and wherein the second control determines the angle of the bend.

Another object of the invention is to provide a control mechanism, system and method of the above character in which the first and second controls can be actuated independently of each other.

Another object of the invention is to provide a control mechanism, system and method of the above character which is user friendly.

Another object of the invention is to provide a control mechanism, system and method of the above character which can be held by a human hand in which the first and second controls can be operated by use of the fingers of the same hand holding the control mechanism.

Additional features and objects of the invention will appear from the following description in which the preferred embodiments are set forth in detail in conjunction with the accompanying drawings.

FIG. 1 is an isometric view showing a control mechanism and system incorporating the present invention.

FIG. 2 is a cross-sectional view taken along the line 2—2 of FIG. 1.

FIG. 3 is an enlarged detail view partially in cross section of the control mechanism shown in FIG. 1 with the top plate removed.

FIG. 6a is a portion of a circuit diagram similar to that shown in FIG. 6 but making provision for both coarse and fine controls.

Figure 4:
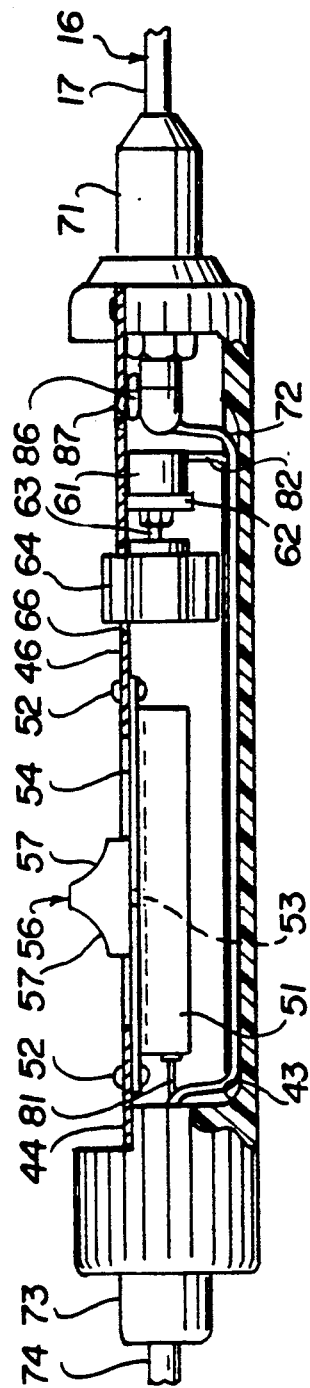
FIG. 4 is a cross-sectional view of the control mechanism shown in FIG. 1.

In general the control system of the present invention consists of a flexible elongate member having proximal and distal extremities and having a plurality of circumferentially spaced-apart elements having a negative coefficient of expansion disposed in the distal extremity. A control mechanism is secured to the proximal extremity of the flexible elongate member. The control mechanism is provided with a housing which is adapted to be grasped by a human hand. A first control member is slidably mounted in the housing and a second control member is rotatably mounted in the housing. The first and second control members are accessible to the fingers of the human hand grasping the housing. Electrical means is provided for coupling the first and second control members to the elements having a negative coefficient of expansion whereby when the first and second control members are moved, the distal extremity of the flexible elongate member is moved in accordance with the positioning of the first and second control members.

More in particular, as shown in the drawings, the control mechanism and system for steering the distal extremity of a flexible elongate member includes a control system 11 and a control mechanism 12. A flexible elongate member 16 is provided which has proximal and distal extremities 17 and 18. The flexible elongate member 16 is formed of a suitable material such as plastic and is provided with a plurality of lumens. As shown in FIG. 2, four of such lumens 21, 22, 23 and 24 have been provided which are spaced apart circumferentially as well as a centrally disposed lumen 26. Flexible elongate elements 31, 32, 33 and 34 are disposed in the lumens 21–24 and have a characteristic which is activated by heat. As disclosed in U.S. Pat. No. 5,238,005, such elements can have a negative coefficient of expansion or alternatively can have a shape-memory. The distal extremities of these elements 31–34 are connected to a common return conductor 36 provided in the lumen 26. The return conductor 36 extends to the proximal extremity 17 of the flexible elongate member 16. Similarly, conductors (not shown) are provided within the flexible elongate member element 16 which are connected to the elements 31–34 having a negative coefficient of expansion and extend through the flexible elongate member to the proximal extremity 17.

The control mechanism 12 is mounted on the proximal extremity 17 of the flexible elongate tubular member 16. It consists of an elongate cylindrical housing 41 which is sized so that it is adapted to fit within the human hand, for example it can have a diameter such as approximately 1" and a length of approximately 6". The housing can be formed of a suitable material such as aluminum or plastic and is provided with fluting 42 extending longitudinally of the housing. The fluting 42 facilitates grasping of the housing so that it will not slip within the hand. The housing 12 is provided with an elongate recess 43 which extends longitudinally of the housing and which opens through a flat surface 44 provided on one side of the housing 41. A flat or planar cover plate 46 is mounted on the surface 44 and covers the recess 43 and is secured to the surface 44 by suitable means such as screws 47.

A device representing linear motion such as a linear potentiometer 51 is mounted in the recess and is secured to the cover plate 46 by suitable means such as a pair of screws 52. The linear potentiometer 51 includes a slider 53 which is adapted to move longitudinally of the potentiometer and which extends through an elongate slot 54 provided in the top cover plate 46 and extending longitudinally of the cylindrical housing 41. A first control member 56 is provided for the housing 41 and is mounted on the slider 53. The control member 56 is provided with opposed arcuate surfaces 57 which are adapted to be engaged by two fingers of the hand.

A device representing rotary motion such as a rotary potentiometer 61 is also provided within the recess 43 of the housing 41 and is mounted on a plate 62 extending transversely in the recess 43 of the housing underlying the top cover plate 46. The rotary potentiometer 61 is provided with a control shaft 63 which extends through the plate and which has mounted thereon a second control member 64 in the form of a rotary knob which extends upwardly through a rectangular slot 66 provided in the cover plate 46. The knob 64 is provided with fluting 67 to facilitate frictional engagement between the knob and the finger of the human hand engaging the knob.

The proximal extremity 17 of the flexible elongate member 16 is secured to the housing 41 by a fitting 71 through which the conductors hereinbefore described extend and are connected to a cable 72 that extends through the recess 43 underlying the rotary potentiometer 61 and the linear potentiometer 51 and through a fitting 73 mounted on the other end of the housing 41. The fitting 73 is connected to a flexible cable 74 which is connected to a connector 76. The connector 76 is removably connected to another connector 77 provided on control console 78. Additional cables 81 and 82 are provided within the housing and are connected to the connector 73 and extend through the cable 74 to the control console 78. A light-emitting diode 86 is provided underlying a hole 87 in the top cover plate 46 to indicate when the power is on.

Figure 5:
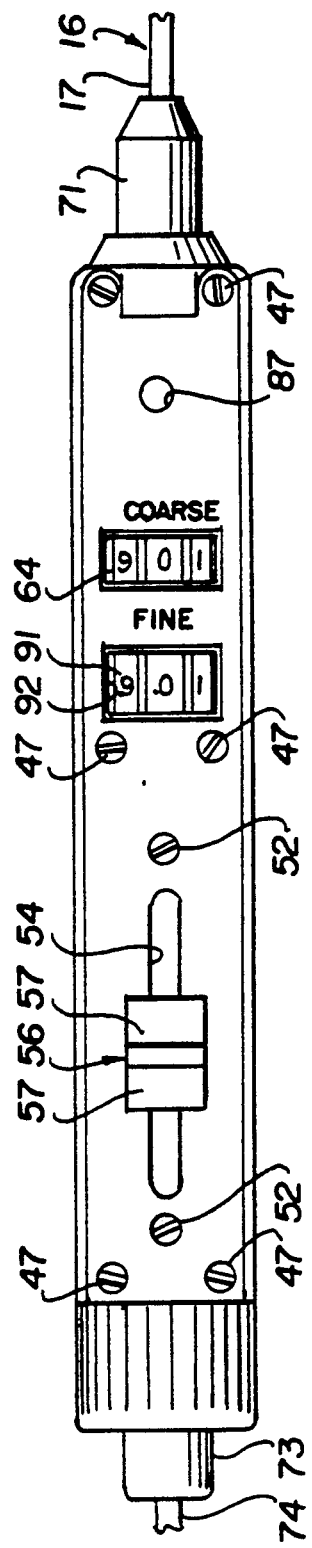
FIG. 5 is a top plan view of an alternative embodiment of a control mechanism showing coarse and fine controls.

Another embodiment of a control mechanism similar as that shown in FIGS. 1, 2, 3 and 4 is shown in FIG. 5 which differs only in that an additional control member 91 has been provided. The control member 91 is in the form of a circular knob as is the control member 64 and extends through another rectangular slot 92 forward of the slot 54 in the cover plate 46. The additional control member 64 is connected to another rotary potentiometer (not shown) in the same manner as the control member or knob 64 is connected so that the control member 64 can provide a coarse adjustment and the control member 91 can provide a fine adjustment for controlling the distal extremity of the flexible elongate tubular member 16.

Figure 6:
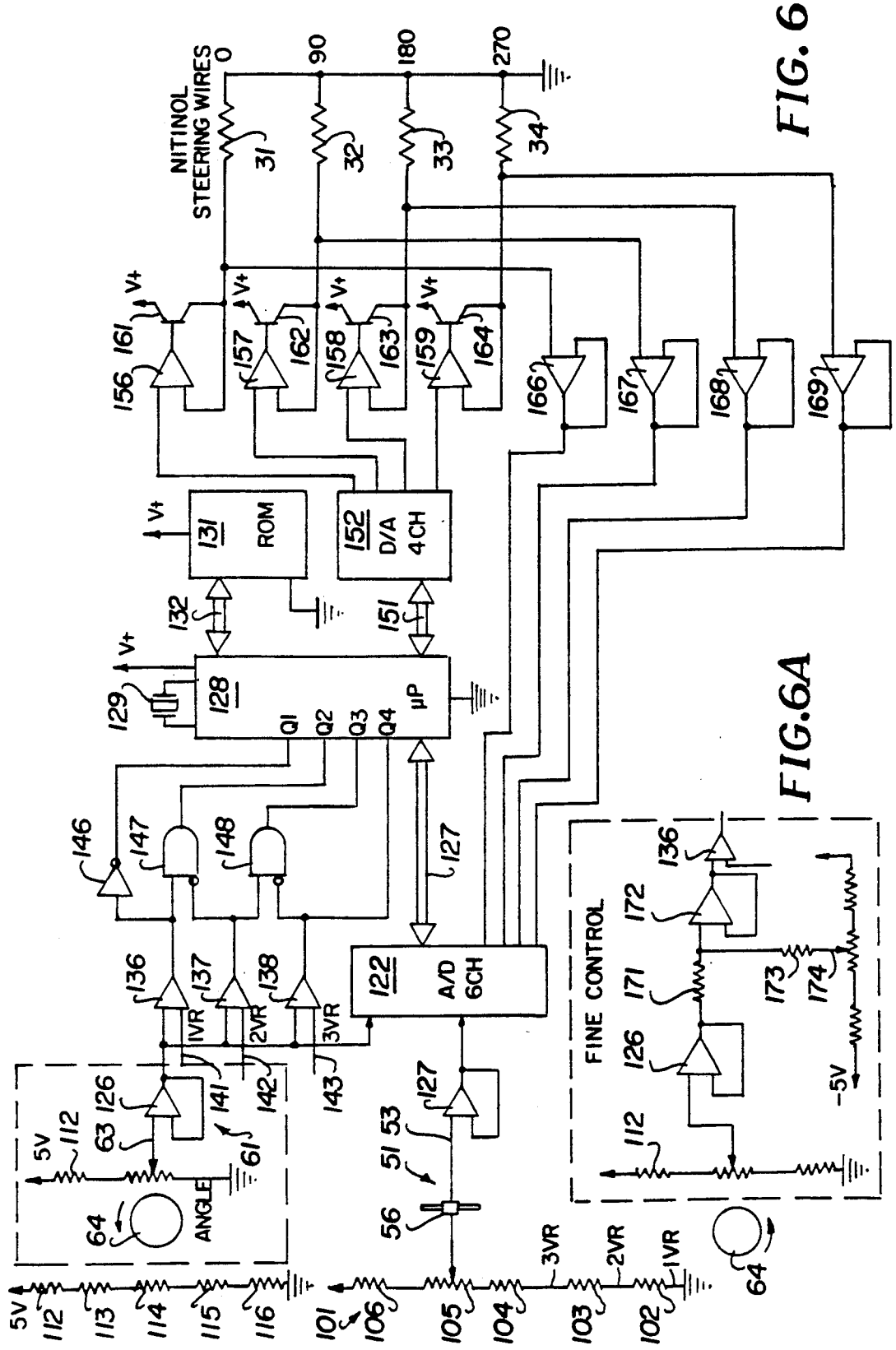
FIG. 6 is a circuit diagram of the electronics in digital form utilized in the control system.

Operation and use of the control mechanism and system in performing the method of the present invention may now be briefly described in conjunction with the digital circuitry which is shown in FIG. 6. As shown in FIG. 6, the digital circuit includes the linear potentiometer 51 which is provided with the wiper 53 engaging or contacting the linear resistance 101 which is connected between ground and a 5-volt supply and can be divided into five separate resistances 101-106 of a suitable value, as for example 10 kilo-ohms to provide a resistor having a total value of 50 kilo-ohms so that there is a 1-volt drop across each resistor starting from ground. The rotary potentiometer 61 which is provided with the wiper 63 engages a resistance of a suitable value, as for example 125 kilo-ohms, which is connected between a 5-volt supply and ground. The potentiometer 61 is divided into five separate resistors 111-116 of 25 kilo-ohms each so that there is a 1-volt drop between each resistor. In rotation of the second control member 64 through 360° of rotation and more, the voltage would be 0 at 0°, 1 volt at 90°, 2 volts at 180°, 3 volts at 270° and 4 volts at 360°, with the voltage again dropping to 0 shortly thereafter at the 0° point to again repeat the progression of voltages. Thus it can be seen that the rotary potentiometer 61 can be moved through 360° and the rotation continued.

Movement of the first control member to position the slider 53 to adjust the bend in the distal extremity of the flexible elongate member 16 produces a voltage which is supplied through a buffer amplifier 121 to a second channel of a six-channel A-to-D converter 122. The output voltage on the wiper 63 of the rotary potentiometer is supplied through the buffer amplifier 126 directly to the first channel of the A-to-D converter 122. The A-to-D converter is connected by a bus 127 to a microprocessor 128 which is controlled by a crystal 129. As shown, the microprocessor 128 is connected to a positive voltage and to ground. It is in communication with a ROM 131 through a bus 132. The ROM is also connected to a positive voltage and ground, as shown.

The microprocessor 128 is also provided with four inputs identified as Q1, Q2, Q3 and Q4 which represent the first, second, third and fourth quadrants for rotational movement of the distal extremity of the flexible elongate member 16. In order for the microprocessor to do its calculations, it must know from an angular standpoint which quadrant the distal extremity 18 of the flexible elongate member 16 is in and in which direction it is moving. Thus, by way of example let it be assumed that the rotary potentiometer is moved through an angle of 45° from 0° to produce 0.5 volt on the wiper 63. This 0.5 volt of information is supplied through the buffer amplifier 126 to three comparators 136, 137 and 138 which are provided with references 141, 142 and 143, respectively. By way of example, the references for the comparator 136 can be 1 volt, for comparator 137, 2 volts, and for comparator 138, 3 volts. Thus, when the output from all three comparators 136, 137 and 138 is low this indicates that the wiper 63 is at an angle of less than 90° and a signal would be supplied through the digital inverter 146 to the Q1 input to the microprocessor 128.

Let it be assumed by way of example that the second control member 64 has been moved to a 135° angle to produce a voltage of 1.5 volts which would mean that the comparator 136 would go high and this output is supplied to AND gate 147 which supplies a voltage to the Q2 input of the microprocessor 128. Similarly, when the second control member 64 is moved into the next quadrant, the output from the comparators 136 and 137 are both high and a voltage is supplied to the AND gate 148 to cause a signal to be supplied to the Q3 input to the microprocessor 128. When the angle of the second control member 64 is greater than 270° the output from the comparators 136, 137 and 138 will all be high and a signal will be supplied to the Q4 input of the microprocessor 128. Each of the AND gates 147 and 148 has one inverting input. The first AND gate 147 takes its inputs from the first and second comparators 136 and 137, and the second AND gate takes its inputs from the second and third comparators 137 and 138. Thus, it can be seen that the four signals supplied on the inputs Q1 through Q4 inform the microprocessor 128 which quadrant the distal extremity or tip of the flexible elongate member 16 is in. The ROM 131 contains a program for the microprocessor and causes the microprocessor to utilize angle information supplied to the microprocessor to calculate the sine and cosine of the angle to multiply it with the amplitude information which has been supplied to it from the linear potentiometer 51.

The information generated by the microprocessor is supplied through a bus 151 to a four channel D/A converter 152 which is connected to four operational amplifiers 156, 157, 158 and 159. These amplifiers drive common emitter transistors 161-164 which serve as constant current sources. These constant current sources are connected directly to the flexible elongate elements 31, 32, 33 and 34 having a negative coefficient of expansion for controlling the distal extremity 18 of the flexible elongate member 16. Thus, it can be seen that the currents which are generated can be utilized for controlling the movement of the distal extremity of the flexible elongate member. In order for the microprocessor 128 to know precisely what currents are to be supplied to the elements 31, 32, 33 and 34, means is provided for sensing the voltages developed across the elements 31-34 and consists of four lines which are connected to the elements 31, 32, 33 and 34 and which are connected to the inputs of buffer amplifiers 166, 167, 168 and 169, the outputs of which are connected into the four remaining channels of the A-to-D converter 122. This makes it possible to monitor the resistance changes in the four elements 31, 32, 33 and 34. The resistance changes in the elements 31, 32, 33 and 34 can be readily measured because of the resistance changes as the elements 31-34 become heated.

When it is desired to provide a fine control for the rotary motion of the digital extremity of the flexible elongate member 16, the circuitry which is shown in FIG. 6A can be provided, in which the coarse control knob 64 covers a coarse range from 0.5 to 3.5 volts and the fine control 91 covers a range from ±0.5 volts so that the total voltage can be varied from 0-4 volts to provide the four quadrants hereinbefore described. The output from the amplifier 126 is supplied through a resistor 171 to one of the inputs of the summing amplifier which has added to it a voltage supplied through a resistor 173 connected to a wiper 174 controlled by the knob 91 of a rotary potentiometer 176 connected between a +5 volts and a −5 volts and divided into five increments of resistance. Thus, a coarse control knob 64 can be utilized for providing a coarse movement of the distal flexible elongate member to the desired approximate position, after which the fine control knob 91 can be utilized to move the tip or distal extremity 18 in a smaller increment to the desired position.

Figure 7:
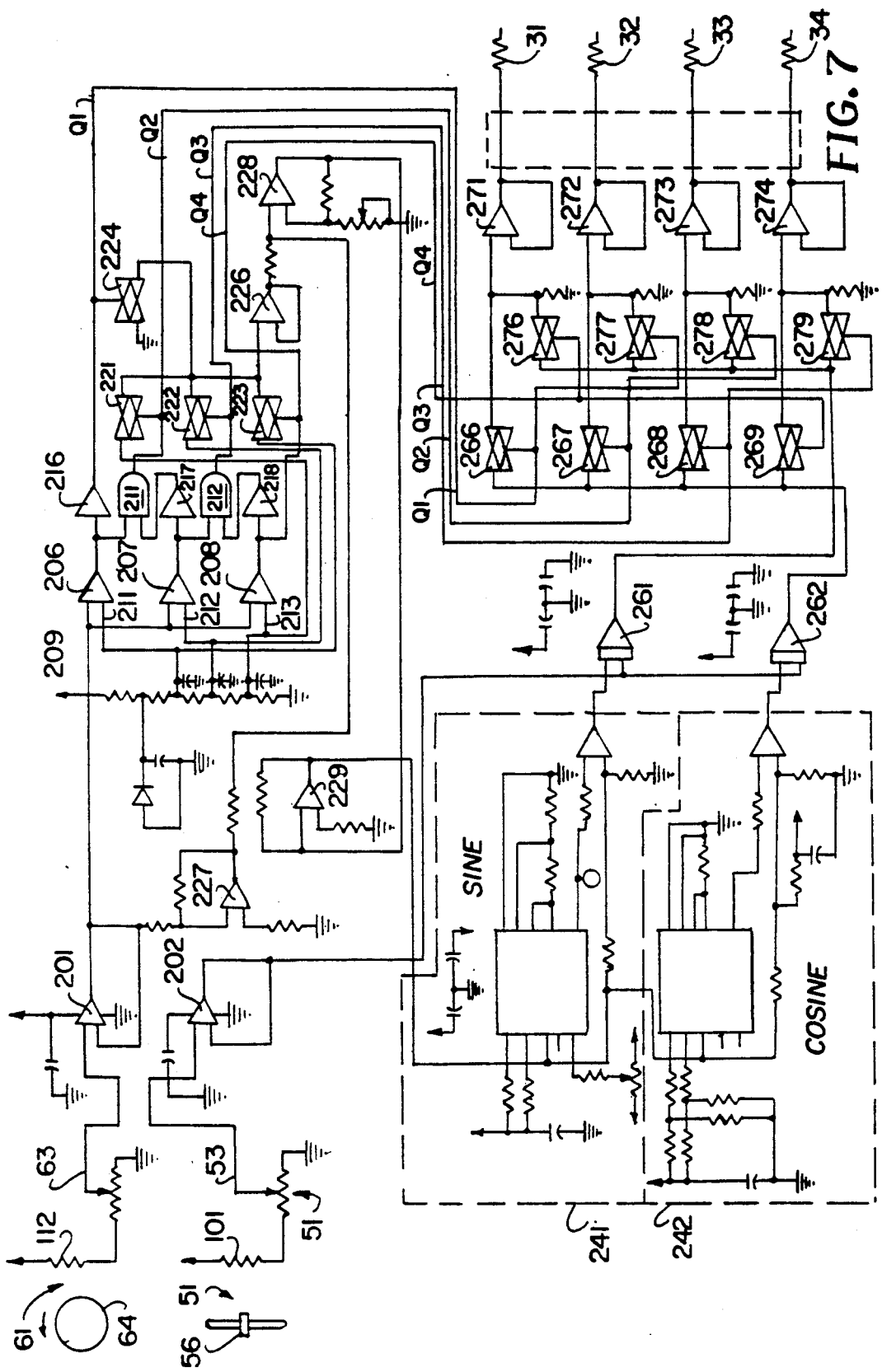
FIG. 7 is a circuit diagram of the electronics in analog form utilized in the control system.

An analog circuit for performing the same functions as performed by the digital circuit shown in FIG. 6 is shown in FIG. 7. The linear potentiometer 51 and the angular potentiometer 63 are connected in a similar manner as in FIG. 6. The output from the angular potentiometer 61 is supplied to a buffer amplifier 201 and, similarly, the output from the linear potentiometer 51 is supplied to a buffer amplifier 202. The output from the buffer amplifier 201 is supplied to three comparators 206, 207 and 208 which, by the logic hereinbefore described in conjunction with FIG. 6, provides four output signals on lines identified as Q1, Q2, Q3 and Q4 to provide the necessary quadrant information which is used to determine which of the four steering elements will be energized. Thus, if the distal extremity 18 of the flexible elongate member 16 is in the first quadrant, only two leads corresponding to Q1 and Q2 will be actuated. If it is in the second quadrant, the leads Q2 and Q3 will be actuated. If it is in the third quadrant, leads Q3 and Q4 will be actuated, and if it is in the fourth quadrant, leads Q4 and Q1 will be actuated. The comparators 206, 207 and 208 are provided with three references 211, 212 and 213 of 1, 2 and 3 volts, respectively, by the voltage divider network 209. The outputs from the comparators 206, 207 and 208 are supplied to AND gates 211 and 212 and three inverters 216, 217 and 218. The quadrant outputs Q through Q4 are connected to the control input of analog switches 221, 222, 223 and 224. The output of the analog switches 221, 222, 223 and 224 are interconnected as shown and provide an input to the buffer amplifier 226. The combined outputs of the analog switches take on a value of 0 V, 1 V, 2 V or 3 V depending on the quadrant that the angular potentiometer 61 is in. The output of the buffer amplifier 226 is added to the output of an inverting amplifier 227 and is supplied to the input of the adding amplifier 228 which has its output supplied to an inverting amplifier 229 which provides a scaled value of the angle to the sine and cosine functions are represented by the circuitry shown in the conventional circuitry in blocks 241 and 242.

The outputs of the sine and cosine function blocks 241 and 242 are supplied to multipliers 261 and 262 which serve to multiply the angle information supplied by the sine and cosine blocks with the amplitude information supplied from the buffer amplifier 202 connected to the linear potentiometer 51. Thus, the output of the amplifier 261 would be sine $\theta$ multiplied by the amplitude. Similarly, the same amplitude is multiplied by the multiplier 262 with cosine $\theta$. The output from the multiplier 262 is supplied to the inputs of analog switches 266, 267, 268 and 269 which have their outputs connected to the inputs of operational power amplifiers 271, 272, 273 and 274. The outputs of these operational amplifiers are connected to the flexible elongate elements 31, 32, 33 and 34 having negative coefficients of expansion. Similarly, the output of the multiplier 261 is connected to the inputs of analog switches 276, 277, 278 and 279 and which also have their outputs connected to the operational amplifiers 271, 272, 273 and 274. The control inputs of the analog switches 266-269 and 276-279 are under the control of the Q1, Q2, Q3 and Q4 leads. Thus, it can be seen that means has been provided for supplying predetermined amounts of energy to the flexible elongate elements 31-34, and thereby controlling the distal extremity of the catheter. The amount of energy supplied to one of these elements is proportional to the value of the A sine $\theta$ or A cosine $\theta$ when A is the amplitude encoded by the linear potentiometer 51 and θ is the angle encoded by the rotary potentiometer 61. Thus, by way of example, the element 31 could be supplied with current proportional to A cosine θ and the element 32 could be supplied with current proportional to A sine θ. As the angle increases, A cosine θ becomes smaller and A sine θ becomes larger. At 90°, for example, A cosine θ is 0 and all of the energy is supplied to the one element 32. Thus it can be seen with the present circuitry, as the rotary potentiometer is moved, the amount of current to be supplied to the elements is calculated on the fly.

It is apparent that from the foregoing that there has been provided a control mechanism system and method for the steering of the distal extremity of a flexible elongate member by which the desired movement of the distal extremity can be accomplished by movement of a slide member and a rotary member representing, respectively, the bending and rotary motion of the distal extremity of the flexible elongate member. The control mechanism and system is user friendly and can be easily operated.

It should also be pointed out that instead of using potentiometers other encoding devices such as capacitive or optical encoders or simply movable wiper contacts engaging stationary contacts can be used. Also the potentiometers can be replaced with three position rocker switches or pushbutton switches, which would allow a counter to count for bending and right or left for rotation. The output of the counter would be directly connected to a microprocessor, or an analog voltage could be provided by connecting the counter to a DA converter.

What is claimed is:

1. A control mechanism for use with a flexible elongate member having proximal and distal extremities and having a plurality of circumferentially spaced-apart elements having a characteristic which is activated by heat disposed in the distal extremity comprising a housing adapted to be grasped by a human hand and coupled to the proximal extremity of the flexible elongate member, a first control member slidably mounted in the housing for linear motion from one linear position to another linear position, a second control member rotatably mounted in the housing for rotary motion from one rotary position to another rotary position, said first and second control members being accessible to the fingers of the human hand grasping the housing and electrical means adapted to couple the first and second control members to the elements in the distal extremity of the flexible elongate member to supply heat to the elements whereby when the first and second control members are moved, the distal extremity of the flexible elongate member is moved in accordance with the positioning of the first and second control members.

2. A control mechanism as in claim 1 together with an additional control member rotatably mounted in the housing and connected to the electrical means so that the second control member and the additional control member can provide coarse and fine controls.

3. A control mechanism as in claim 1 wherein said electrical means includes a linear motion output device connected to the first control member and providing an electrical output corresponding to the linear position of the first control member which is positionable to select a desired amount of bend for the distal extremity of the flexible elongate member and a rotary motion output device connected to the second control member and providing an electrical output corresponding to the rotary position of the second control member which is positionable to select a desired angle for the distal extremity of the flexible elongate member, means for calculating the sine and cosine of the selected desired angle of the rotary motion output device, means for calculating the value of the selected desired bend of the linear motion output device, multiplier means for combining the values of the sine and cosine of the selected angle and the value of the selected bend and means connected to the multiplier means for supplying electrical energy to cause heat to be supplied to the elements to cause movement of the distal extremity of the flexible elongate member in accordance with the combined values.

4. A system as in claim 3 together with logic means connected to the output of the rotary motion output device for determining in which of four quadrants the distal extremity of the flexible elongate member is disposed and providing a quadrant output, and wherein said means for calculating the sine and cosine of the selected desired angle includes means connected to the logic means receiving the quadrant output so that the sine and cosine are calculated for that quadrant.

5. A system as in claim 3 wherein said elements are resistive elements and wherein said electrical means includes means for sensing the resistive values of the elements to adjust the amount of current which is supplied to the elements in accordance with the sensed values of resistance.

6. A system as in claim 1 wherein said electrical means is in digital form.

7. A system as in claim 1 wherein said electrical means is in analog form.

8. A method for steering the distal extremity of a flexible elongate member by the use of a control mechanism having a first movable control member of a linear motion output device and a second movable control member of a rotary motion output device comprising generating an electrical signal corresponding to a selected linear position of the first control member, generating an electrical signal corresponding to the selected angular position of the second control member, utilizing electrical logic means to determine in which quadrant of four quadrants the distal extremity of the flexible elongate element is located, generating sine and cosine functions of the selected angle in accordance with the quadrant, multiplying the signal representing the selected angular position with the signal representing the selected linear position to provide a combined signal and controlling the positioning of the distal extremity of the flexible elongate member in accordance with the combined signal.

9. A method for controlling the distal extremity of a flexible elongate element by the use of a control mechanism coupled to the proximal extremity of the flexible elongate member, the control mechanism having a first electrical device having a first control member for providing a desired bend in the distal extremity and a second electrical device having a second control member for providing a desired angle in the distal extremity comprising causing the distal extremity to bend in accordance with the first control member and causing rotational movement of the distal extremity of the flexible elongate member in accordance with the second control member regardless of the rotational position of the control mechanism.

* * * * *